ic Patent [19]

United States Patent [19]

Mabire et al.

[11] Patent Number: 4,650,877
[45] Date of Patent: Mar. 17, 1987

[54] PROCESS FOR PRODUCING 4,5-DIHYDROXY-2-IMIDAZOLIDINONES

[75] Inventors: Frédéric Mabire; Alain Blanc, both of Paris, France

[73] Assignee: Societe Francaise Hoechst, Puteaux, France

[21] Appl. No.: 664,793

[22] Filed: Oct. 25, 1984

[30] Foreign Application Priority Data

Nov. 8, 1983 [FR] France .................. 83 17702

[51] Int. Cl.$^4$ ........................................ C07D 233/40
[52] U.S. Cl. ................................................. 548/319
[58] Field of Search ........................ 548/307, 311, 319

[56] References Cited

U.S. PATENT DOCUMENTS

| | | | |
|---|---|---|---|
| 2,731,472 | 1/1956 | Reibnitz | 548/319 |
| 3,091,617 | 5/1963 | Burris | 548/319 |
| 3,260,565 | 7/1966 | Beachem | 548/319 |
| 3,433,799 | 3/1969 | Huber | 548/307 |
| 4,173,645 | 11/1979 | Enders et al. | 548/319 |

Primary Examiner—Richard A. Schwartz
Assistant Examiner—Kurt G. Briscoe
Attorney, Agent, or Firm—Browdy and Neimark

[57] ABSTRACT

The invention concerns a process for producing cyclic ureas of the general formula (II):

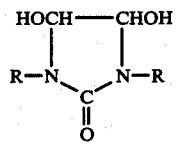

(II)

in which R is selected from the group comprising hydrogen atom and $C_1$-$C_4$ alkyl radicals through condensation in aqueous medium at a pH of between 4 and 7 and at a temperature of between 40° and 60° C. of glyoxal with or without excess of a urea having the general formula (I):

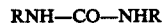

RNH—CO—NHR    (I)

in which R has the same meaning as above, said process being conducted in the presence of a catalytic amount of orthophosphoric acid.

5 Claims, No Drawings

PROCESS FOR PRODUCING 4,5-DIHYDROXY-2-IMIDAZOLIDINONES

This invention relates to a process for producing cyclic ureas of imidazolidinic structure and application thereof.

The cyclic ureas of imidazolidinic and particularly 4,5-dihydroxy-2-imidazolidinone, hereinafter called DHEU, and 4,5-dihydroxy-1,3-dimethyl-2-imidazolidinone, hereinafter called DM$_e$DHEU are raw materials currently used for preparing textile sizings for uncreasibility and unshrinkability treatments of cellulosic tissues.

For the last years, such sizings have become of significant industrial importance so that searches are constantly continued to obtain more performing, less costly sizings, that do not yellow upon chlorine treatments, stable to household washings, free of any secondary effects liable to affect the quality of the sized tissue. A solution to this problem consists of being able to manufacture at small costs those cyclic ureas of imidazolidinic structure, pure, either in aqueous solutions or in the crystallized state.

It is known to produce such cyclic ureas of imidazolidinic structure through condensation of glyoxal with a urea having the general formula (I)

in which R represents a hydrogen atom or a C$_1$–C$_4$-alkyl radical.

Such cyclic ureas having the general formula (II):

in which R has the same meaning as given above such as DHEU, DM$_e$DHEU, are known and described in crystallized form (Sidney L. Vail et Al. J. Org. Chem., 1965, 30, 2179–2182).

These authors were even able to isolate in the crystallized state the cis- and the trans-DM$_e$DHEU.

However, such cyclic ureas having the general formula (II) are obtained in the crystallized state with low yields even after long condensation periods between the glyoxal and the ureas having the general formula (I).

As a matter of fact, it is known that condensation of glyoxal with ureas is complex and that, depending on the operative conditions, the cyclization process may stop at the desired primary dihydroxylated addition step (Sidney L. Vail et Al., Amer. Dyestuff Reporter, 1961, 550–553; U.S. Pat. No. 2,731,472, No. 3,260,565, No. 3,304,312) or may be continued either by a double cyclization up to glycolurile: [4,5-d]-tetrahydroimidazo-(1H,3H)-imidazole-2,5-dione (J. NEMATOLLANI et Al., J. Org. Chem., 1963, 28, 2378–2380; H. BLITZ et Al., Ber., 1907, 40, 4808) or by a double symmetric condensation with untransformed glyoxal up to 1,2-bis(4,5-dihydroxy-2-oxo-1-imidazolidinyl)-1,2-dihydroxy-ethane (E. KANSCHEV et Al., Textilveredelung, 1981, 16, 414–417). Other deviations are also observable such as formation of hydantoin (H. PAULY et Al., Ber., 1930 63, 2063–2069) or degradation of glyoxal according to Cannizzaro.

Moreover, the cylic ureas having the general formula (II) present a cis-trans-geometric isomerism at the carbon atoms substituted by the hydroxy groups and it is admitted today that condensation of glyoxal with a urea having the general formula (I) is not stereoselective and that there is formed at least in a first time as much cis-isomer as trans-isomer, then that such balance is shifted to the most stable trans-form (Sidney L. Vail et Al., J. Org. Chem., 1965 30, 2179–2182).

Consequently, in processes for preparation of cyclic ureas having the general formula (II), through condensation of glyoxal with suitably substituted urea, the yield of the desired cyclic urea, on the one hand, and on the other hand, its tendency to crystallize in its reactional medium depends upon very numerous factors, the main factor recognized as such in the state of the art being the condensation pH which must be either of between 4 and 8 (J. G. FRICK et Al., Ing. and Eng. Chem., Product Research and Development, 1982, 21, 599–600) or stabilized at a value of between 4 and 6.8 by a buffer in adequate quantity (U.S. Pat. No. 4,295,846).

However, the Applicants surprisingly discovered that the use in a catalytic quantity of orthophosphoric acid in the known processes for preparation of cyclic ureas having the general formula (II) through condensation, in aqueous medium at a pH of between 4 and 7 and at a temperature lower than 60° C., of glyoxal with the suitably substituted ureas having the general formula (I) improves the expected condensation rate, significantly reduces the rate of the secondary interferring reactions and permits to increase the yields of the desired pure cyclic ureas either crystallized or raw in solution in its reactional medium.

This invention, therefore, relates to a process for producing cyclic ureas having the general formula (II) through condensation of glyoxal with a urea having the general formula (I) in excess or not in an aqueous medium presenting a pH of between 4 and 7, and at a temperature of between 40° C. and 60° C., characterized by the fact that it is conducted in the presence of a catalytic quantity of orthophosphoric acid.

According to the invention the process is more especially intended for producing cyclic ureas having the general formula (II) in which R represents a hydrogen atom or a methyl radical.

The quantity of orthophosphoric acid used in the process according to the invention may vary in significant enough proportions depending on the reactional parameters and/or the nature of the reactives. Experience shows that the higher the contents of orthophosphoric acid the quicker the reaction rate. However, from a concentration higher than 150 mmoles of orthophosphoric acid per mole of glyoxal used, the yield of the desired cyclic urea isolated at the crystallized state is no longer modified and even has the tendency of decreasing if such concentration increases.

Consequently, a good compromise is to be found when carrying out the process according to the invention, with from 2 to 150 mmoles of orthophosphoric acid per mole of glyoxal used.

According to preferred conditions for carrying out the invention, for the preparation of cyclic ureas having the general formula (II) in which R represents a hydrogen atom or a methyl radical, the above-described process is conducted in the presence of 20 to 60 mmoles of orthophosphoric acid per mole of glyoxal used.

Investigations realized by following up the condensation rates between glyoxal hereinafter designated as G, and the urea, hereinafter designated as U, on the one hand, and on the other hand, between the glyoxal and the N,N'-dimethylurea, hereinafter designated as DM$_e$U, effected either without catalyst or in the presence of buffer substances such as citric acid and its salts, sodium acetate, or finally, in the presence of orthophosphoric acid, have permitted to reveal a double advantage in an orthophosphoric acid catalysis according to the invention, namely, acceleration of the condensation reaction rate expected and secondly slowing down of the interferring condensation rates of the cyclic ureas formed having the general formula (II) in which R represents a hydrogen atom with untransformed glyoxal.

These reaction rates have been determined from test samples taken at regular time intervals in the reactional media either by thermal differential analysis ATD, or by high pressure liquid chromatography HPLC, or by chemical dosage of the free glyoxal.

Thus, the following experimental facts have been brought to the fore; they are mentioned in the following Table and collected in the condensation of one mole of glyoxal in aqueous solution at 40% by weight with one mole of urea effected at pH=6 and at 40° C. either without catalyst, such test being designated as (a) or in the presence of 7.14 mmoles of monohydrated citric acid, and 48.8 mmoles of sodium acetate, such test being designated as (a), or finally in the presence of 28.5 mmoles of orthophosphoric acid, in solution at 85% by weight in water, on the one hand, and on the other hand, in the condensation of one mole of glyoxal in aqueous solution at 40% by weight with 1.07 moles of N,N'-di-methylurea effected at pH=6, and at 40° C., either without catalyst, this being the test (d), or finally in the presence of 28.5 mmoles of acid and 39 mmoles of sodium acetate, this being test (e), or finally, in the presence of 28.5 mmoles of orthophosphoric acid in aqueous solution at 85% by weight, this being test (f).

TABLE

|  | DHEU | | | DM$_e$DHEU | | |
|---|---|---|---|---|---|---|
|  | test a | test b | test c | test d | test e | test f |
| ΔH kcal/mole | 4.9 | 4.5 | 5.1 | 8.0 | 9.5 | 12.7 |
| EA kcal/mole | 19.1 | 23.2 | 19.8 | 25.6 | 14.8 | 15.5 |
| log$_e$ k s$^{-1}$ | 23 | 30 | 26 | 30 | 16 | 18 |
| speed constant k 1 mole$^{-1}$min$^{-1}$ | 0.0015 | 0.0025 | 0.0097 | 0.00029 | 0.0076 | 0.01 |
| relative speed | 1 | 1.7 | 6.5 | 1 | 26 | 34 |

Therefore analysis of such Table reveals a clear acceleration of the condensation rate of the glyoxal either with urea or N,N'-dimethylurea when one proceeds according to the invention in the presence of orthophosphoric acid, and that such catalytic effect if still significative when the condensation is effected in the presence of buffer substances such as the citric acid and sodium acetate couple.

Moreover, the influence of orthophosphoric acid upon the secondary interferring condensation rate of glyoxal, one secondary reaction afraid of, was determined. To this end, 1 mole of glyoxal in aqueous solution at 40% by weight was reacted at pH=6 and at 40° C. with one mole of DHEU either without catalyst, test (g) or in the presence of 60 mmoles of orthophosphoric acid in an aqueous solution at 85% by weight, test (h), according to test (g), the speed constant is $6.1.10^{-2}$ moles.1.min$^{-1}$, and according to test (h) it is of $1.210^{-2}$ mole.1$^{-1}$.min.$^{-1}$, i.e. 5 times slower.

It can moreover be noted that in the absence of orthophosphoric acid such secondary reaction is about 40 times quicker than the main reaction of glyoxal with urea, whereas in the presence of catalytic quantity of orthophosphoric acid, it is only 1.2 times quicker. Therefore, there has been disclosed the double advantage of orthophosphoric acid catalysis as mentioned previously.

Experience also shows that the condensation rate of glyoxal with urea having the general formula (I) is the quicker, the higher the temperature of the reactional medium. However, above 60° C. the higher the temperature, the more colored the reactional medium is, thereby resulting at the formed cyclic urea having the general formula (II) in the occurrence of disturbing colorations and a steading yield or even sometimes a lower yield than that obtained at a temperature lower than 60° C.

As can be expected, there can also be noted that by conducting the process according to the invention with an excess of urea having the general formula (I) relative to the glyoxal used, the consumption of glyoxal and the yield of the desired cyclic urea are simultaneously enhanced. However, too high an excess of free urea in the reactional medium is harmful to the crystallization of the desired cyclic urea, on the one hand, and on the other hand, to the use of the raw reactional medium for the preparation of textile sizings.

Consequently, and as known otherwise, the process according to the invention is carried out with a molar ratio of glyoxal to urea having the general formula (I) included between 0.6 and 1. According to preferred conditions, this molar ratio of glyoxal to urea of general formula (I) is 0.75 when R represents a hydrogen atom and 0.935 when R represents a methyl radical.

In this type of condensation the influence of pH is also known and significant. A pH lower than 4 flavors bicondensation of urea having the general formula (I) with glyoxal and leads to bicyclic structures of the glycolurile type and a pH higher than 7 leads to cyclic colored ureas having the general formula (II) as well as degradation of glyoxal by Cannizzaro's reaction.

The process according to the invention is therefore carried out at a pH of between 4 and 7, preferably, at a pH of between 5.8 and 7.0.

The cyclic ureas having the general formula (II) are soluble in water i.e. DHEU presents a solubility in water at 20° C. of 28 g in 100 g of water and DM$_e$DHEU a solubility under the same conditions of 64 g in 100 g of water. As to the reactives i.e. glyoxal and orthophosphoric acid, they are marketed in aqueous solution, the first usually at 40% by weight and the second commonly at 85% by weight. The ureas having the general formula (I) are also soluble in water. Consequently, the process according to this invention as realized in aqueous medium is carried out starting from these commercial reactives, without additional introduction of water thereinto and after completion of the reaction, if it is desired to isolate at the crystallized state the desired cyclic ureas having the general formula (II) it is generally necessary to eliminate under vacuum at a temperature lower than 50° C. part of water supplied by the aqueous solution of glyoxal used.

Either in the cystallized state or the raw state, i.e. in solution in their preparation medium, the cyclic ureas having the general formula (II) obtained according to the process of this invention can be used among other for obtaining textile sizings, as is described in U.S. Pat. No. 3,260,565. In particular, they may be etherified by an alkanol having the general formula (III)

$$(R_1OH \qquad \qquad (III)$$

in which $R_1$ represents a $C_1$–$C_4$-alkyl radical according to methods known in themselves so as to lead to cyclic ureas having the general formula (IV):

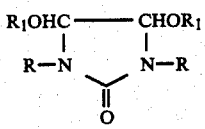

in which R and $R_1$ have the same meanings as above.

These cyclic ureas having the general formula (IV) are raw materials suitable for preparing textile sizings.

Other advantages and characteristics of this invention will appear from the following description and the examples given by way of illustration and not at all limitatively.

EXAMPLE 1

There is heated at 40° C. under stirring at pH=5.8 the following solutions obtained by mixing in this order:
678 g (4.67 moles) of glyoxal in aqueous solution at 40% by weight,
12.6g (109 mmoles) of orthophosphoric acid in aqueous solution at 85% by weight,
15 g (176 mmoles) of sodium hydroxide in aqueous solution at 47% by weight,
440 g (5 moles) of N,N'-dimethylurea.

In this step, depending on the acidity of the commercial aqueous solution of glyoxal used, it is sometimes required to modulate the quantity of soda introduced therein to obtain the pH of 5.8.

After 4 hours heating at 40° C. there is obtained a limpid solution presenting a concentration by weight of free glyoxal of 0.2%, i.e. 40 mmoles and a transformation rate of 99.1%. Chromatographic analysis of the reactional medium through HPLC reveals that it only contains, apart from water and mineral products, the desired DM$_e$DHEU, about 59%, i.e. 4.63 moles, glyoxal, 0.2%, i.e. 40 mmoles, and DM$_e$U, 2.84%, i.e. 370 mmoles.

The reactional medium is then left for 15 hours at the ambient temperature. The desired DM$_e$DHEU spontaneously crystallizes. It is squeezed out, then dried, in a ventilated incubator to constant weight at 50° C.

Thus, there is isolated a first crop of 500 g (3.42 moles) of DM$_e$DHEU presenting a melting point of 142° C.

The mother-waters, i.e. 645 g, are concentrated to 445 g under vacuum at a temperature lower than 50° C., they they are left for crystallization for 15 hours. There is thus isolated a second crop of 95 g (0.65 mole) of DM$_e$DHEU having a melting point of 142° C. without pressure decrease in admixture with the first crop.

Both crops are combined and there is thus obtained 595 g (4.07 moles) of trans-4,5-dihydroxy-1,3-dimethyl-2-imidazolidinone, colorless, crystallized, presenting a melting point of 142° C., and a nuclear magnetic resonance of proton spectrum at 60 MHz in solution in heavy water in accordance with the proposed structure:
4.9 ppm, s, 2H (CH); 2.9 ppm, s, 6H (N—CH$_3$).

This product presents a solubility at 20° C. of 64 g in 100 g of water. The total yield is set to 87.2% of the theoretical value as calculated relative to the glyoxal used.

COMPARATIVE EXAMPLE 1A

There is heated at 40° C. under stirring at pH=5.8 the following solution obtained by mixing in this order:
g (4.67 moles) of glyoxal in aqueous solution at 40% by weight,
4.62 g (22 mmoles) of monohydrated citric acid,
15 g (182 mmoles) of anhydrous sodium acetate,
440 g (5 moles) of N,N'-dimethylurea.

In this step, the pH is set as necessary to 5.8 by addition thereto of soda at 47% by weight.

After 4 hours of heating at 40° C. the clear solution obtained presents a free glyoxal contents of 2.95% by weight, i.e. 579 mmoles and a transformation rate of 87.8%.

The reactional medium is thereafter treated as in Example 1 and there is thus isolated 50 g (0.343 mole) of DM$_e$DHEU colorless, crystallized, presenting a melting point of 142° C. i.e. a yield of 7% of the theoretical value as calculated relative to the glyoxal used.

COMPARATIVE EXAMPLE 1B

There is heated at 40° C. under stirring at pH=5.8 the following solution obtained by mixing in this order:
678 g (4.67 moles) of glyoxal in aqueous solution at 40% by weight,
12.6 g (109 mmoles) of orthophosphoric acid in aqueous solution at 85% by weight,
4.62 g (22 mmoles) of monohydrated citric acid,
15 g (182 mmoles) of anhydrous sodium acetate,
15 g (176 mmoles) of sodium hydroxide in aqueous solution at 47% by weight,
440 g (5 moles) of N,N'-dimethylurea.

In this step, the pH is set as necessary to 5.8 by modulating the quantity of soda introduced therein.

After 4 hours of heating at 40° C. the clear solution obtained presents a free glyoxal contents of 0.2% i.e. 40 mmoles and a transformation yield of 99.1%.

The reactional medium is thereafter treated as in Example 1 and there is thus isolated 300 g (2.05 moles) of the DM$_e$DHEU, colorless, crystallized, presenting a melting point of 142° C., i.e. a yield of 44% of the theoretical value as calculated relative to the glyoxal used.

EXAMPLE 2

There is heated at 50° C. under stirring at pH=7 a solution obtained by mixing in this order:
145 g (1 mole) of glyoxal in aqueous solution at 40% by weight;
6.6 g (57 mmoles) of orthophosphoric acid in aqueous solution at 85% by weight,
80 g (1.33 moles) of urea,
qs of sodium hydroxide in aqueous solution at 47% to obtain a pH=7.

After 2 hours of heating at 50° C., the clear solution obtained presents a zero content of free glyoxal.

The reactional medium is then left at the ambient temperature for 15 hours. The desired DHEU crystallizes spontaneously, it is squeezed out, then dried at constant weight in a ventilated oven at 50° C.

Thus, there is isolated a first crop of 73.2 g (0.62 moles) of crystallized DHEU, colorless, presenting a melting point of 140° C.

Through concentration of the mother-waters at 120 g under vacuum at a temperature lower than 50° C., there is isolated a second crop of 12 g (0.1 mole) of DHEU, crystallized, colorless, presenting a melting point of 142° C. without pressure decrease in admixture with the first crop.

Both crops are combined. Thus, there is obtained 85.2 g (0.72 mole) of crystallized trans-4,5-dihydroxy-2-imidazolidinone having a melting point of 142° C. and a nuclear magnetic proton resonance at 60 MHz in heavy water in agreement with the proposed structure: 5.1 ppm, s, 2H (CH). The yield is set to 72% of the theoretical value as calculated relative to the glyoxal used.

The DHEU presents an aqueous solubility at 20° C. of 28 g in 100 cm³ of water.

EXAMPLE 3

There is heated at 40° C. under stirring at pH=6.0 a solution obtained by mixing in this order:

725 g (5 moles) of glyoxal in solution at 40% by weight in water, 33 g (286 mmoles) of orthophosphoric acid in aqueous solution at 85% by weight, 34.5 g (405 mmoles) of sodium hydroxide in aqueous solution at 47% by weight, 300 g (5 moles) of urea.

In this step, the quantity of soda introduced therein can be modified as necessary to obtain the selected pH=6.0.

After 5 hours of heating, a clear solution is obtained, with a concentration by weight of free glyoxal of 2.5% i.e. 471 mmoles. The reactional medium is then left at the ambient temperature, then it is treated as in Example 2. Thus, there is isolated 252 g (2.13 moles) of trans-DHEU having a melting point of 142° C. The total yield is set to 42.6% of the theoretical value as calculated relative to the glyoxal used.

COMPARATIVE EXAMPLE 3A

There is heated at 40° C. under stirring at pH=6.0 a solution obtained by mixing in this order:

725 g (5 moles) of glyoxal in aqueous solution at 40% by weight, 8.2 g (39 mmoles) of monohydrated citric acid, 20.1 g (245 mmoles) of anhydrous sodium acetate, 300 g (5 moles) of urea.

In this step, depending on the acidity of the commercial aqueous solution of glyoxal, the pH is set if necessary to 6.0 by adding soda at 47% by weight thereto.

After 5 hours of heating, a clear aqueous solution is obtained, with a concentration by weight of free glyoxal of 3.3% i.e. 600 mmoles.

Thereafter the reactional medium is left at the ambient temperature, then it is treated as in Example 3. Thus, there is isolated 122 g (1.034 moles) of trans-DHEU, having a melting point of 142° C. The yield is set to 20.7% of the theoretical value as calculated relative to the glyoxal used.

We claim:

1. A process for producing a cyclic urea of the formula (II):

wherein R is selected from the group consisting of hydrogen and $C_1-C_4$ alkyl radicals by condensing, in an aqueous medium at a pH of from about 4 to about 7 and at a temperature of from about 40° to about 60° C., glyoxal with urea of the formula (I);

wherein R has the same meaning as above the improvement comprising conducting the process in the presence of a catalytic amount of orthophosphoric acid.

2. A process according to claim 1 wherein the catalytic amount of orthophosphoric acid used is between 2 mmoles and 150 mmoles per mole of glyoxal used.

3. A process according to claim 1, wherein the urea of the general formula (I) is urea.

4. A process according to claim 1, wherein the urea of the general formula (I) is N,N'-dimethylurea.

5. A process according to claim 1, wherein the catalytic amount of orthophosphoric acid is of between 20 mmoles and 60 mmoles per mole of glyoxal used.

* * * * *